United States Patent [19]

Di Battista et al.

[11] 4,317,767

[45] Mar. 2, 1982

[54] STABILIZERS FOR POLYMERS AND POLYMERS STABILIZED THEREBY

[75] Inventors: Piero Di Battista; Francesco Gratani, both of Milan, Italy

[73] Assignee: Montedison S.p.A., Milan, Italy

[21] Appl. No.: 116,850

[22] Filed: Jan. 30, 1980

[30] Foreign Application Priority Data

Feb. 1, 1979 [IT] Italy .............................. 19761 A/79

[51] Int. Cl.$^3$ .............................................. C08K 5/34
[52] U.S. Cl. .................................... 524/102; 546/190
[58] Field of Search ................................. 260/45.8 NP

[56] References Cited

U.S. PATENT DOCUMENTS

| 3,543,306 | 11/1970 | Biland | 260/45.8 NP |
| 3,940,363 | 2/1976 | Murayama et al. | 260/45.8 NP |
| 3,975,357 | 8/1976 | Murayama et al. | 260/45.8 NP |
| 4,148,784 | 4/1979 | Malherbe et al. | 260/45.8 NP |
| 4,197,236 | 4/1980 | Rosenberger et al. | 260/45.8 NP |

Primary Examiner—John Kight, III
Assistant Examiner—R. A. White

[57] ABSTRACT

New N-alkyl-piperidine derivatives of hydroxy-benzyl-malonic acid are disclosed. These new compounds are useful for stabilizing thermoplastic polymers, in partcular polyole fins, against sunlight, heat and oxidation.

A process for producing the new compounds is also disclosed, as well as the use thereof as stabilizers of polymers and polymeric compositions.

11 Claims, No Drawings

STABILIZERS FOR POLYMERS AND POLYMERS STABILIZED THEREBY

THE PRIOR ART

As is known, the synthetic polymers in general suffer a certain degradation of their chemical physical properties when they are exposed to atmospheric agents or when subjected to heat-treatments both during processing and use thereof.

It is also known and usual, to add stabilizing substances to the synthetic polymers in order to improve their thermo- and photo-oxidative stability. For this purpose use is generally made of anti-oxidizers, light stabilizers or mixture of them.

It is known, too, that the compounds containing the 2,2,6,6-tetra-alkyl-piperidine group have excellent anti-oxidizing properties. In particular, U.S. Pat. No. 3,640,928 describes the esters of 2,2,6,6-tetra-alkyl-piperidine and British Specification No. 1,442,100 describes the esters of 2,2,6,6-tetra-alkyl-piperidine with mono- or di(hydroxybenzyl) malonic acid, as light and ageing stabilizers of thermoplastic polymers.

Said piperidine derivatives even if they perform a certain stabilizing action, that in some cases is satisfying, do not entirely solve all the problems connected with the stabilization of the polymers.

THE PRESENT INVENTION

An object of this invention is to provide a new class of stabilizers containing 2,2,6,6-tetra-alkyl-piperidine group, which are more effective than the prior-art stabilizers, in protecting the thermoplastic synthetic polymers against oxidation.

This and other objects are achieved by this invention in accordance with which the thermoplastic synthetic polymers are stabilized by new N-alkyl-piperidine derivatives of hydroxy-benzyl-malonic acid having the general formula

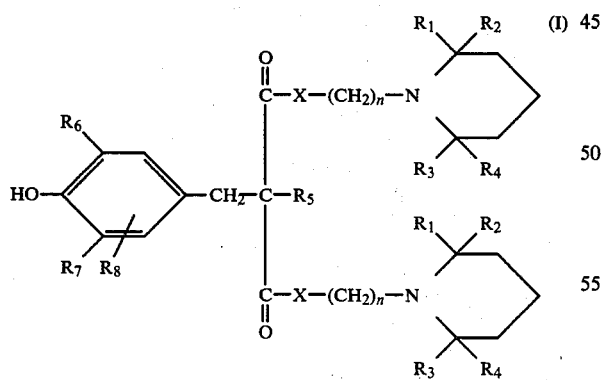

wherein:
each of $R_1$, $R_2$, $R_3$ and $R_4$, which may be the same or different, is an alkyl radical having 1 to 6 carbon atoms or $R_1$ and $R_2$ together and $R_3$ and $R_4$ together form a cycloalkyl radical having from 5 to 8 carbon atoms; $R_5$ is hydrogen, an alkyl radical having 1 to 18 carbon atoms or a hydroxy-benzyl group of the formula:

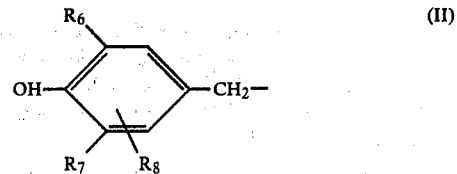

each of $R_6$ and $R_7$, which may be the same or different, is hydrogen, an alkyl radical having from 1 to 6 carbon atoms, an aralkyl radical having 7 to 9 carbon atoms, or a cycloalkyl radical having 5 to 8 carbon atoms; $R_8$ is hydrogen or an alkyl radical having 1 to 6 carbon atoms; n is an integer comprised between 1 and 12 and X is oxygen or

group, wherein $R_9$ is hydrogen, an alkyl radical having 1 to 18 carbon atoms, an alkenyl radical having 3 or 4 carbon atoms, a cycloalkyl radical having 4 to 12 carbon atoms, an aryl radical having 6 to 12 carbon atoms or an aralkyl radical having 7 to 9 carbon atoms.

The presently preferred N-alkyl-piperidine derivatives of hydroxy-benzyl-malonic acid having generally formula (I) for use in the practice of the present invention are those in which $R_1$, $R_2$, $R_3$ and $R_4$ are each methyl, $R_5$ is butyl or hydroxy-benzyl of general formula II, $R_6$ and $R_7$ are each tert.butyl, $R_8$ is hydrogen, X is oxygen and n is an integer comprised between 2 and 6.

The N-alkyl-piperidine derivatives of hydroxy-benzyl-malonic acid of general formula (I), may be synthetized according to various methods which consist in carrying out a series of known reactions, in different sequences.

Thus, for instance, the compounds of the present invention having general formula (I) may be synthetized by reacting the hydroxy-benzyl malonic acid or one of its reactive derivatives, for instance an ester, with a 2,2,6,6-tetra-alkyl-1-alkanol-piperidine or a 1-alkylene-amine-2,2,6,6-tetra-alkyl-piperidine according to the scheme:

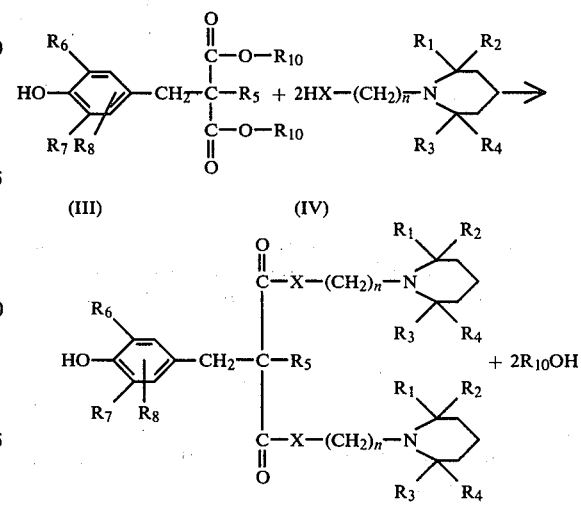

wherein $R_{10}$ is hydrogen or an alkyl radical having 1 to 4 carbon atoms.

The esterification reaction, the trans-esterification or the amidation reaction may be carried out in the presence of any catalyst known for such a reaction, such as: lithium hydroxide, di-butyl-tin oxide, sodium methylate, manganese carbonate, etc.

Product (III) may be synthetized according to any known method such as, for instance, by reacting the di-alkyl-benzyl-amine with an alkyl malonate, according to the scheme:

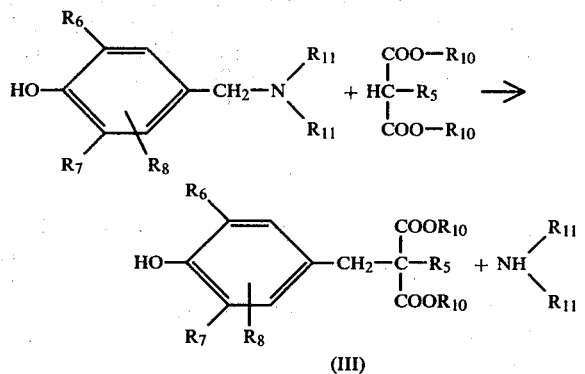

wherein $R_{11}$ is an alkyl group having from 1 to 4 carbon atoms.

The reaction is carried out in the presence of strong bases derived from an alkaline metal such as, for instance alkoxides, hydrides, amides of sodium or lithium.

Product (IV) may easily be synthetized according to the following scheme:

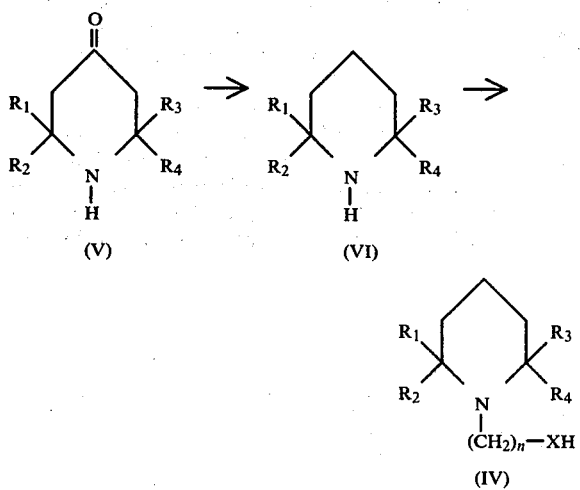

Wherein:
Reaction (V)→(VI) is carried out by reduction according to any known method such as, for instance, the Clemmensen method, the Wolff Kischner method or by hydrogen in the presence of a catalyst.

The reaction (VI)→(IV) is carried out by reacting piperidine (VI) with an ω-halogenated alcohol in the presence of a base such as a hydroxide of an alkaline or earth-alkaline metal, a hydride, an amide or an alkoxide of an alkaline metal.

The derivatives having "X" equal to

may be synthetized by converting the hydroxyl group to an amine group, according to any known method, such as for instance by treatment with $P Br_3$ and subsequent treatment with ammonia or an amine.

The derivatives of general formula (I) are used, according to the present invention, as stabilizers for organic materials usually subject to deterioration or degradation by the action of oxygen, light and heat.

Organic materials that may preferably be stabilized by the compounds according to the invention, are all the thermoplastic synthetic polymers, which includes:
polyolefins including the homopolymers of olefins such as low and high density polyethylene, polypropylene, polystyrene, polybutadiene, polyisoprene and the like, and copolymers of olefins with other ethylenically unsaturated monomers such as ethylene-propylene copolymers, ethylene-butene copolymers, ethylene-vinylacetate copolymemers, styrene-butadiene copolymers, styrene-acrylonitrile copolymers and acrylonitrile-styrene-butadiene copolymers;
polyvinyl chloride and polyvinylidene chloride, including both the homopolymers and copolymers of vinyl chloride and vinylidene chloride with each other or each with vinyl acetate or other ethylenically unsaturated monomers;
polyacetals such as polyoxymethylene and polyoxyethylene;
polyesters such as polyethylene-terephthalates;
polyamides such as nylon 6, nylon 6-6 and nylon 6-10;
polyurethanes;
polycarbonates;
butadiene/styrene copolymers;
natural and synthetic rubbers, etc.

Such polymers may be used either as powder or granules, or as shaped articles such as for instance: fibers, films, sheets and other shaped articles, and also as latex and foams.

The presently preferred synthetic polymers for use in practice of this invention are the polyolefins deriving from monomers of the general formula: $R—CH=CH_2$ wherein R is an alkyl or aryl group, or a hydrogen atom.

The presently preferred polyolefin is polypropylene consisting prevailingly of isotactic macromolecules and obtained by polymerization of propylene in the presence of a stereospecific catalyst.

The N-alkyl-piperidine derivatives of hydroxy-benzyl-malonic acid, of the general formula (I), is added to the thermoplastic synthetic polymer to be stabilized, according to this invention, in an amount sufficient to prevent degradation of the polymer.

This amount can vary in a wide range as a function of type, properties and particular uses of the stabilized polymer. Generally said derivatives can be added to the polymer in amounts comprised between 0.01 and 5.0% by weight, based on the polymer Weight; in practice, however, the effective amount varies as a function of the type of polymer to be stabilized. Thus, for instance, in the case of polyolefins an effective amount can range from 0.01 to 2% by weight; in the case of polyvinyl chloride and of polyvinylidene chloride such amount can vary from 0.01 to 1% by weight; while in the case of polyurethanes and the polyamides the effective amount varies from 0.01 to 5% by weight.

The stabilizers of general formula (I) may be used either alone or in admixture with other known additives such as antioxidants, ultraviolet-ray adsorbents, pigments, fillers, basic nitrogen-containing polycondensates, stabilizers, etc. Some examples of such additives are: oxy-benzo-triazols, oxy-benzo-phenones, Ni-stabilizers, metal soaps, phenolic antioxidants, phosphites, thioesters, hydroquinone derivatives, triazine compounds, acyl-amino-phenols, benzyl-phosphonates, etc.

Such additives may be used together with the N-alkyl-piperidine derivatives of hydroxy-benzyl malonic acid having general formula (I), according to this invention, at a ratio by weight ranging from 0.5:1 to 3:1.

The incorporation of the N-alkyl-piperidine derivatives of general formula (I) or of the mixture containing said derivatives with the synthetic polymer, may be carried out according to different conventional procedures and at any stage prior to or during the manufacturing of the shaped article from the polymer.

Thus, for instance, the additives in powder form can be simply mixed with the polymer, under stirring, or the polymer can be mixed with a solution of the stabilizers in a suitable solvent, whereupon said solvent is evaporated; or the stabilizers can be added to the polymer at the end of polymerization.

Moreover, the stabilizing effect can be achieved by applying the stabilizer on the manufactured article, for instance by immersing the article in a solution or dispersion of the stabilizers and by successively evaporating the solvent or dispersant.

The following non-limiting examples are given for a more detailed understanding of the present invention and for enabling the artisan to practice the same. Unless otherwise specified, all the parts in the examples are to be understood as parts by weight.

EXAMPLE 1

Preparation of 2(3.5 di-ter-butyl-4-hydroxy-benzyl)2-n.butyl-malonate of di-[N-ethyl(2,2,6,6-tetramethyl)piperidine]

In a 250 cc flask, equipped with a stirrer, a heating sleeve and a thermometer, 42.3 g (0.3 mols) of 2,2,6,6-tetra-methyl-piperidine, dissolved in 50 cc methanol, and 24.15 g (0.3 mols) of 2-chloro-ethanol, were introduced.

This mixture was stirred for 2 hours and then heated for 8 hours at the reflux-temperature of the solvent, still under constant stirring. During the whole time of the heating, 12 g of NaOH (0.3 mols) in tablets were gradually added to the mixture. Following the addition of NaOH, the mass was stirred for a further 2 hours, after which the reaction mixture was cooled down and filtered. The filtrate was dried to evaporate the methanol and the residue was crystallized in cyclohexane.

40 g (yield 72%) of a white product, in the form of needles, were obtained, having a melt point 95°–97° C.

The elemental analysis of the obtained product gave the following results: C=71.27%; N=7.55%; H=12.50%.

The elemental analysis and the N.M.R. spectrum, correspond to the compound:

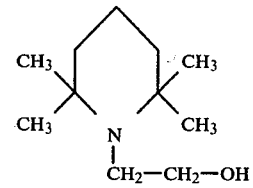

having the following centesimal calculated composition: C=71.30%; H=12.51%; N=7.56%.

In a 50 cc flask, 3.7 g of the compound so obtained were added to 4.35 g of (n.butyl) (3,5-di-ter.butyl-4-hydroxy-benzyl) ethyl malonate.

The mixture was thereupon brought to melting and 0.02 g of LiH, as a catalyst, were added thereto. The mixture was maintained, under stirring, for 3 hours at 140°–160° C. and then at 150°–160° C. for 90 minutes under vacuum at a residual pressure of 50 mmHg, and for further 60 minutes at 150°–160° C., at a residual pressure of 17 mmHg.

The resulting product was then cooled down, dissolved in CHCl$_3$ and washed with water containing a few drops of acetic acid.

After separation of the organic solution and evaporation of the solvent, the residue was crystallized in hexane. 7 g of a white product in the form of a powder were obtained, having a melt point of 98°–100° C. and 100° C. The elemental analysis of the obtained product gave the following results: C=74.08%; H=10.72%; N=3.90%.

The elemental analysis and the N.M.R. spectrum, correspond to the compound:

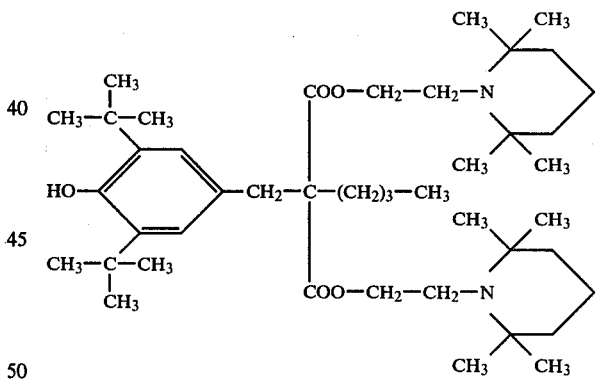

having the following centesimal calculated composition: C=74.11%; H=10.74%; N=3.93%.

STABILIZATION TESTS 200 cc of chloroform containing, dissolved therein, 2(3,5 di-ter.butyl-4-hydroxy-benzyl)2n.butyl malonate of di-[N-ethyl-(2,2,6,6-tetramethyl)piperidine], as prepared in Example 1 and in amounts as indicated in Table 1, were added to 300 g of non-stabilized polypropylene (having an intrinsic viscosity, measured in tetraline at 130° C., of 162 cc/g, a residue after extraction of the crude polymerizate with n-heptane of 96.5%, and ashes=80 ppm).

Each mixture was stirred for about 6 hours at room temperature, in a rotary evaporator and then dried at 50° C., at 0.01 mm Hg for 1 hour. The additioned powder so obtained was extruded in a Brabender extruder at 220° C. and granulated. The granules were molded to films and small plates at 200° C. for 3 minutes between two square steel plates measuring 20 cm×20 cm, under a load of 1000 kg.

The films so obtained exhibited a uniform thickness of 50-60 microns and the small plates of 1 mm thick and were practically colorless and homogeneous. On the films so produced, the thermo-oxidative and photo-oxidative stabilities were determined.

As thermo-oxidative stability values were taken:

(a1) the induction period (Ip) of the thermo-oxidation at 170° C. and at 760 mmHg of oxygen, intended as the time required to get a quick increase of the oxygen absorption rate, and (b1) the resistance to ageing in an oven, intended as the time (T.I.) required to evidence, to the naked eye, on the examined test piece, any cracks of chalking of the surface and other modifications of the same, after exposure of the test piece in an oven at 150° C. in air current.

As photo-oxidative stability values were taken:

(a2) the induction period (Ip) of the photo-oxidation, intended as the time necessary to get a rapid increase in the formation rate of the carbonyl groups, and (b2) the embrittling time of the test piece, determined by bend-breaking tests.

To determine the thermo-oxidative stability, 0.2 g of the above obtained films were cut to pieces and introduced into a cell of about 50 cm³ wherein an oxygen atmosphere was created by repeatedly removing and introducing oxygen. The cell was connected with an oxygen-measuring means equipped with a recorder of absorbed volumes.

The cell was immersed into a thermostatic bath maintained at a temperature of 170° C.

The induction period (Ip) values, measured on the films, are recorded in Table 1.

To determine the photo-oxidative degradation, some cut pieces of film were mounted on the proper supports of apparatus Xenotest 1200 and exposed to the light of Xenon lamps at maximum U.V. exposure (quartz cylinder and mirrors).

The temperature in the exposure chamber was maintained at 45°±2° C. and at a relative humidity of 50%±5%. At intervals of time, film samples were drawn in order to measure the I.R. absorption in correspondance with the wave length of 1720 cm$^{-1}$, corresponding to the absorption of the carbonyl groups.

To evaluate the concentration of the carbonyl groups, a conventional value for the molar absorption coefficient equal to 300 l/mol×cm was assumed. The induction period values (Ip) measured on the films, are recorded in Table 1.

The exposure time to the Xenotest, necessary to cause the rupture of the film by one bending only, was taken as embrittling time.

TABLE 1

| Stablilizer % by weight | Thermo-oxidative stability | | Photo-oxidative stability | |
|---|---|---|---|---|
| | Ip in hours | Embrittling time in hours | Ip in hours | Embrittling time in hours |
| — | 0 | <24 | 40 | 60 |
| 0.30 | 2.7 | 380 | 850 | 1000 |
| 0.50 | 4.2 | 550 | 1300 | 1400 |

EXAMPLE 2

Preparation of 2,2'di(3,5-di-ter.butyl-4-hydroxy-benzyl)malonate of di[N-ethyl(2,2,6,6-tetramethyl)piperidine]

By operating according to Example 1, 3.70 g of N-ethanol-2,2,6,6-tetramethyl piperidine were reacted with 5.98 g of 2,2'di(3,5-di-ter.butyl-4-hydroxy-benzyl) ethyl-malonate.

6.5 grams of a product were obtained in the form of a white powder having a melt point 196°-198° C.

The elemental analysis of the obtained product gave the following results: C=75.46%; H=10.36%; N=3.19%.

The elemental analysis and the N.M.R. spectrum correspond to the compound:

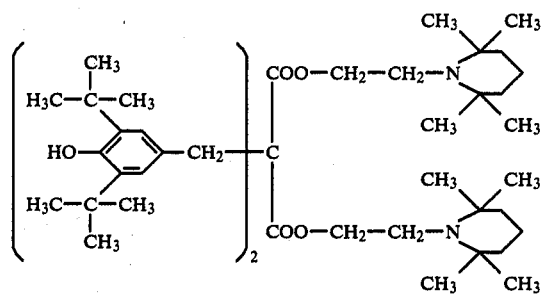

having the following centesimal calculated composition: C=75.47%; H=10.36%; N=3.20%.

STABILIZATION TESTS

By operating according to Example 1, films having uniform thicknesses of from 5 to 60 microns were prepared. The samples were subjected to thermo-oxidative and photo-oxidative stability tests of Example 1. The obtained results are recorded in Table 2:

TABLE 2

| Stabilizer % by weight | Thermo-oxidative stability | | Photo-oxidative stability | |
|---|---|---|---|---|
| | Ip in hours | Embrittling time in hours | Ip in hours | Embrittling time in hours |
| 0.3 | 6.0 | 600 | 250 | 350 |
| 0.5 | 10.3 | 900 | 400 | 480 |
| 1 | 18 | 1800 | 500 | 750 |

What we claim is:

1. Compositions comprising synthetic thermoplastic polymers stabilized to oxidation, heat and light, and having incorporated therein, in an amount sufficient to prevent degradation of the polymer, a N-alkyl-piperidine derivative of the hydroxy-benzyl-malonic acid having formula

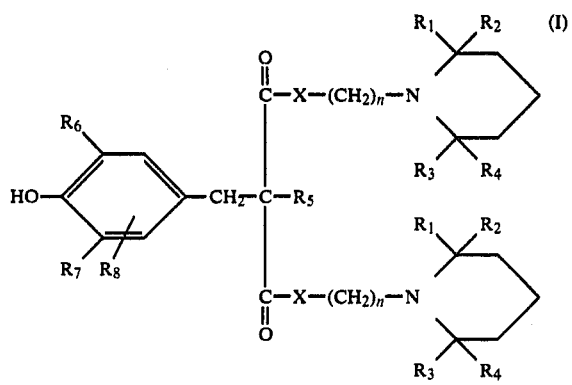

wherein each of $R_1$, $R_2$, $R_3$ and $R_4$, which may be the same or different, is an alkyl radical having 1 to 6 carbon atoms or $R_1$ and $R_2$ together and $R_3$ and $R_4$ together form a cycloalkyl radical having 5 to 8 carbon atoms; $R_5$ is hydrogen, an alkyl radical having 1 to 18 carbon atoms or a 4-hydroxy-benzyl group of the formula

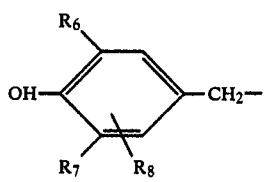

in which of $R_6$ and $R_7$, which may be the same or different, is hydrogen, an alkyl radical having 1 to 6 carbon atoms, an aralkyl radical having 7 to 9 carbon atoms or a cyclo alkyl radical having 5 to 8 carbon atoms; $R_8$ is hydrogen or an alkyl radical having 1 to 6 carbon atoms; n is an integer comprised between 1 and 12, and X is oxygen or

group, wherein $R_9$ is hydrogen, an alkyl radical having 1 to 18 carbon atoms, an alkenyl radical having 3 to 4 carbon atoms, a cyclo-alkyl radical having 4 to 12 carbon atoms, an aryl radical having 6 to 12 carbon atoms or an aralkyl radical having 7 to 9 carbon atoms.

2. Compositions according to claim 1, in which, in formula (I) $R_1$, $R_2$, $R_3$ and $R_4$ are each methyl, $R_5$ is butyl or hydroxybenzyl of formula:

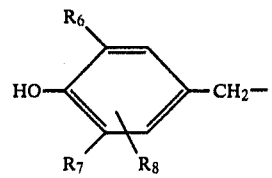

in which $R_6$ and $R_7$ are each tert.butyl, $R_8$ is hydrogen, X is oxygen and n is an integer from 2 to 6.

3. Compositions according to claim 1, in which the N-alkyl-piperidine derivative of hydroxy-benzyl-malonic acid of formula (I) is present in an amount ranging from 0.01 to 5% by weight of the weight of the polymer.

4. Compositions according to claim 1, in which the thermoplastic synthetic polymer is a polyolefin.

5. Compositions according to claim 4, in which the compound of formula (I) is present in an amount ranging from 0.01 to 2% by weight on the weight of the polyolefin.

6. Compositions according to claim 1 in which the thermoplastic synthetic polymer is polyvinyl chloride or polyvinylidene chloride.

7. Compositions according to claim 6, in which the compound of formula (I) is contained in an amount ranging from 0.01 to 1% by weight on the weight of the polymer.

8. Compositions according to claim 1, in which the thermoplastic synthetic polymer is a polyurethane or a polyamide.

9. Compositions according to claim 8, in which the compound of formula (I), is contained in an amount ranging from 0.01 to 5% by weight on the weight of the polymer.

10. Compositions according to claim 1, in which the compound of formula I is employed in admixture with at least one additive selected from the group consisting of oxy-benzo-triazoles, oxy-benzo-phenones, Ni stabilizers, metal soaps, phenolic antioxidants, phosphites, thioesters, hydroquinone derivatives, triazines, acyl-amino-phenols and benzyl-phosphonates.

11. Compositions according to claim 10, in which the ratio by weight of additive or additives to the compound of formula (I) is from 0.5:1 to 3:1.

* * * * *